United States Patent [19]

Levy et al.

[11] Patent Number: 4,513,088
[45] Date of Patent: Apr. 23, 1985

[54] ASSAY FOR MONOCLONAL ANTIBODY AGAINST SURFACE IG OF A HUMAN B CELL TUMOR

[75] Inventors: Ronald Levy, Stanford; David G. Maloney, Palo Alto; Kristiaan Thielemans, Stanford, all of Calif.

[73] Assignee: The Board of Trustees of The Leland Stanford Junior University, Stanford, Calif.

[21] Appl. No.: 480,478

[22] Filed: Mar. 30, 1983

[51] Int. Cl.³ .............................................. G01N 33/54
[52] U.S. Cl. .................................... 436/518; 436/528; 436/531; 436/548; 436/804; 436/813; 436/823; 435/4; 435/7; 435/28; 435/68; 435/172.2; 435/240; 435/259; 435/948; 935/92
[58] Field of Search ............... 436/513, 518, 528, 531, 436/533, 534, 543, 547, 548, 804, 813, 823; 435/4, 7, 28, 68, 70, 172, 240, 259, 948, 172.2; 935/90, 92

[56] References Cited

U.S. PATENT DOCUMENTS 4,267,270  5/1981  Stout ........................................ 435/7

OTHER PUBLICATIONS

Van Camp, B. et al., Protides of the Biological Fluids, vol. B, 1, pp. 279–282, (1983).
Lanier, L. L. et al., J. Immunol., vol. 125, pp. 1730–1736, (1980).
Krolick, K. A. et al., Immunol. Rev., vol. 48, pp. 81–106, (1979).
De Waele, M. A. et al., Brit. J. Haematol., vol. 48, pp. 95–101, (1981).
Bast, E. et al., Clin. Exp. Immunol., vol. 47, pp. 677–682, (1982).
Van Camp, B. et al., Clin. Exp. Immunol. vol. 44, pp. 82–89, (1981).
Levy, R. et al., *Malignant Lymphomas*, Academic Press, N.Y., (1982), pp. 95–106, Rosenberg et al., ed.
Morahan, G., J. Immunolog. Methods, vol. 57, pp. 165–170, (2–1983).
Stevenson, D. et al., Immunology, vol. 41(2), pp. 313–321, (10–1980).
Maloney, D. G. et al., Federation Proceedings: FASEB, vol. 40(3/2), p. 1134, abstract 5137, (1981).
Maloney, D. G. et al., Fed. Proc.: FASEB, vol. 41(3), p. 309, abstract 239(1982).
Bluestone, J. A. et al., J. Immunology, vol. 129(5), pp. 2066–2068, (11–1982).
Engvall, E. et al., Biochimica et Biophysica Acta., vol. 251, pp. 427–435, (1971).
Brown, S. et al., J. Immunology, vol. 125(3), pp. 1037–1043, (9–1980).
Douillard, J. Y. et al., J. Immun. Methods, vol. 39, pp. 309–316, (12–1980).
Cobbold, S. P. et al., J. Immun. Methods, vol. 44, pp. 125–133, (7–1981).
Grutzmann, R. et al., European J. Immunology, vol. 12, pp. 307–312, (4–1982).
Mayumi, M. et al., J. Immunology, vol. 129(2), pp. 904–910, (8–1982).
Stocker, J. W. et al., J. Immun. Methods, vol. 26(1), pp. 87–96, (3–1979).

(List continued on next page.)

*Primary Examiner*—Christine M. Nucker
*Assistant Examiner*—M. Morkowitz
*Attorney, Agent, or Firm*—Ciotti & Murashige

[57] ABSTRACT

An assay that facilitates screening of hybridoma culture media for monoclonal anti-idiotype antibodies, particularly murine monoclonal antibodies that are useful for treating human B cell tumors is disclosed. The assay is a solid phase type assay and involves: incubating a lysate of the patient's B cell tumor with immobilized anti-human Ig; separating unbound lysate materials; incubating the remaining immobilized complex with the test culture medium; separating unbound culture medium material; and incubating the remaining immobilized complex with a labeled anti-mouse Ig; separating unbound labeled anti-mouse Ig; and detecting the presence of label in the remaining immobilized complex.

10 Claims, 3 Drawing Figures

OTHER PUBLICATIONS

Raschke, W. C. et al., Proc. Natl. Acad. Sci., USA, vol. 76(7), pp. 3469–3473, (7-1979).

Hatzubai, A. et al., J. Immunology, vol. 126(6), pp. 2397–2402, (6-1981).

Stites, D. P., Clinical Laboratory Methods for Detection of Antigens and Antibodies, pp. 371–373.

Raschke, W. C. et al., Assembly and Secretion of Pentameric IgM in a Fusion between a Nonsecreting B Cell Lymphoma and an IgG-Secreting Plasmacytoma, pp. 3469–3473.

Mayumi, M. et al., Studies on the Clonal Origin of Human B Cell Leukemia Using Monoclonal Anti-Idiotype Antibodies, pp. 904–910, J. of Immunology, vol. 129, (1982).

Cobbold, S. P. et al., A Rapid Solid-Phase Enzyme-Linked Binding Assay for Screening Monoclonal Antibodies to Cell Surface Antigens, pp. 125–133.

Douillard, J. Y. et al., Enzyme-Linked Immunosorbent Assay for Screening Monoclonal Antibody Production: Use of Intact Cells as Antigen, pp. 309–316.

Stocker, J. W. et al., Methods for Binding Cells to Plastic: Application to a Solid-Phase Radioimmunoassay for Cell Surface Antigens, pp. 87–95.

Brown, S. et al., Immunoglobulin Secretion by Mouse X Human Hybridomas: An Approach for the Production of Anti-Idiotype Reagents Useful in Monitoring Patients with B Cell Lymphoma, pp. 1037–1043, 1980).

Ser. No. 322,377, Monoclonal Anti-Idiotype Antibodies, 11/17/81.

Ser. No. 342,883, Process for Making Monoclonal Anti-Idiotype Antibodies, 01/26/82.

FIG. 3.

ASSAY FOR MONOCLONAL ANTIBODY AGAINST SURFACE IG OF A HUMAN B CELL TUMOR

REFERENCE TO GOVERNMENT GRANT OR CONTRACT

The invention described herein was made in the course of work under a grant or contract from the National Institutes of Health.

DESCRIPTION

1. Technical Field

This invention relates to the field of immunotherapy. More particularly, it relates to an immunoassay that is used in producing monoclonal antibodies against human B cell tumor immunoglobulin (Ig), to identify hybridomas that produce such antibodies.

2. Background Art

Copending, commonly owned U.S. patent applications Ser. Nos. 322,377 and 342,883, filed Nov. 18, 1981 and Jan. 26, 1982, respectively, describe the preparation of murine monoclonal IgG antibodies against the surface Ig of human B cell tumors and the use of those anti-idiotype antibodies to treat and diagnose human B cell malignancies. Therapy using these antibodies has effected total remission of a patient with a B cell lymphoma. Unfortunately, the preparation and identification of the antibodies is a laborious, lengthy process that has limited the use of the method severely.

Much of the laboratory research concerning this mode of treating human B cell malignancies has been directed to improving the procedure for making the antibodies. The method used initially (see U.S. Ser. No. 322,377, supra) started with a fusion of the patient's malignant B cells with a murine myeloma line to "rescue" the secretion of the idiotype (the surface Ig on the patient's tumor cells). Idiotype was collected from the resulting hybridomas and used to immunize mice. Antibody-producing cells (e.g., spleen cells) from the immunized mice were then fused with a murine myeloma line to produce hybridomas. The hybridomas were cloned and culture media were assayed for the presence of anti-idiotype antibody. A solid phase radioimmunoassay (RIA) using idiotype collected from the first hybridomas was used to screen the hybridoma culture media. Hybridomas showing a positive medium were subcloned and used to produce the monoclonal anti-idiotype antibody used in the therapy.

This initial method was replaced with a method that used the B cell tumor x murine myeloma hybridomas directly as an immunogen for immunizing the mice to produce anti-idiotype Ig-producing fusion partners. This reduced the amount of time required to produce antibody because it eliminated the time needed to culture the hybridomas and collect idiotype to use as an immunogen. The B cell tumor x murine myeloma hybridomas were, nonetheless, cultured to produce idiotype for use in the RIA screen of hybridoma culture media.

The next improvement in the process involved using the patient's B cell tumors directly as an immunogen rather than the B cell tumor x murine myeloma hybridomas. Mayumi, M., et al, *J. Immun.* 129:904–910 (1982). It was surprising that this immunization worked because it was believed that the concentration of idiotype in the whole cells was not sufficient to be immunogenic or would not produce a sufficiently large population of anti-idiotype producing fusion partners. This improvement again shortened the time required to make monoclonal anti-idiotype producing hybridomas. The initial fusion to produce idiotype secreting hybridomas as a source of idiotype for use in the RIA screen of hybridoma culture media was, however, still carried out.

A main object of the present invention is to provide a method of assaying the hybridoma culture media for monoclonal anti-idiotype that avoids the need for the initial fusion of the patient's tumor cells with murine myeloma cells to rescue idiotype secretion and collection of idiotype from the fused cells.

DISCLOSURE OF THE INVENTION

The invention is an immunoassay for detecting a monoclonal antibody against the surface Ig of a human B cell tumor in a hybridoma culture medium suspected of containing the monoclonal antibody comprising:

(a) incubating a lysate of cells of the tumor with an immobilized antibody that reacts with the surface Ig but not with the monoclonal antibody;

(b) incubating the incubation product of (a) with the hybridoma culture medium;

(c) incubating the incubation product of (b) with a labeled antibody against the monoclonal antibody; and (d) detecting the presence of labeled complex in the incubation product of (c).

BRIEF DESCRIPTION OF THE DRAWINGS

In the drawings:

FIG. 3 is a chart also showing the specificity of the assay.

MODES FOR CARRYING OUT THE INVENTION

The Idiotype

Figure 1:
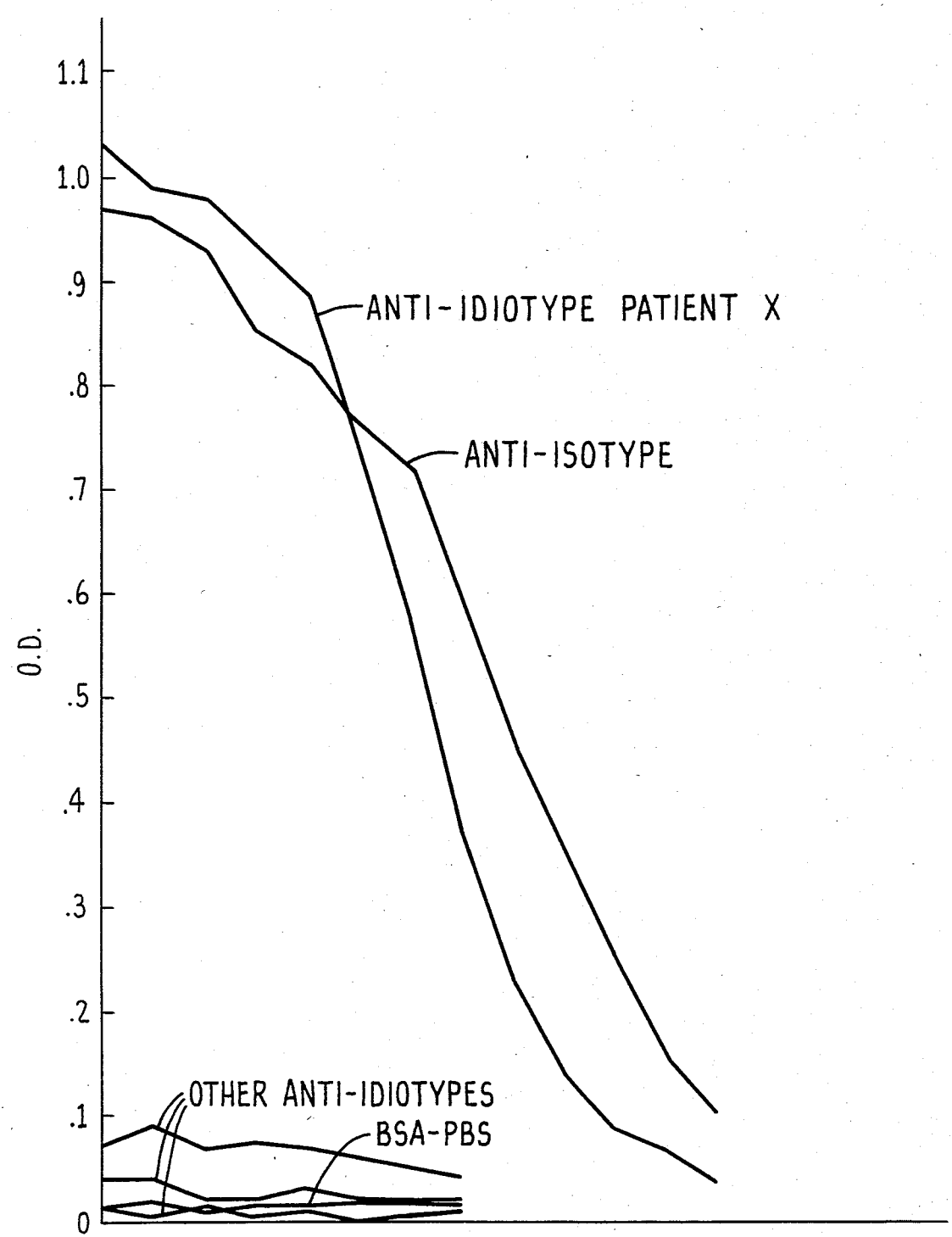
FIG. 1 is a graph showing the results of an assay described in the examples, infra.

About 80% of adult lymphoproliferative malignancies involve Ig-containing or Ig-producing tumors. These tumors, called B cell tumors, include those associated with leukemias and lymphomas such as chronic lymphocytic leukemia, lymphosarcoma cell leukemia, nodular lymphoma, large-cell lymphoma, Burkitt's lymphoma, hairy-cell leukemia, "undifferentiated" lymphoma, and acute lymphocytic leukemia of pre-B cell type. The tumor cell populations of these cancers are clonal in nature and appear to contain cells arrested in various stages of differentiation with respect to Ig synthesis and secretion. Because the tumor population is monoclonal, the Ig produced by the population is likewise monoclonal. That is, the Ig that is expressed or secreted is restricted to a single $V_H$ and $V_L$ region and to a single light chain of either the $\kappa$ or $\lambda$ type. It is usually of the IgM class ($\mu$ heavy chain). The heavy and light chains are typically combined as full homogenous IgM pentamers.

Production of Monoclonal Anti-Idiotype Antibody

The methods for producing murine monoclonal antibodies against the surface Ig of human B cell malignancies are described briefly under "Background Art", supra. As indicated, the preferred method involves using the patient's malignant B cells as an immunogen. The following describes this preferred method.

Malignant human B cells may be isolated from peripheral blood or from a biopsy specimen and stored by conventional procedures. These cells may be used directly as an immunogen. In such use the cells will typically be suspended in physiological saline (e.g., phosphate buffered saline (PBS)) and injected intraperitoneally into the mice at about $10^6$ to $10^7$ cells per injection. The mice are usually injected at least twice with the booster coming about one week after the initial inoculation. Alternatively, the cells may be lysed with lysis buffer, centrifuged to remove cellular debris, and the lysate used as an immunogen instead of whole cells. If desired, the lysate may be purified by affinity chromatography by passing it through an anti-human Ig column. The beads or other column packing may be used as the immunogen or the Ig may be eluted therefrom and the eluate used as immunogen. Spleen cells or other antibody-producing cells are taken from the immunized mice about three days after the final booster inoculation.

The spleen cells are fused with an appropriate murine myeloma cell line using the somatic cell hybridization technique first described by Kohler, G. and Milstein, C., *Nature*, 256:495-497 (1975). Appropriate myeloma lines are those that fuse efficiently, do not secrete contaminating Ig, and support synthesis and secretion of Ig by its spleen cell fusion partner. Examples of such lines are those derived from the original MOPC-21 or MPC-11 mouse tumors that are available from the Salk Institute, Cell Distribution Center, P.O. Box 1809, San Diego, Calif. 92112. The fusion is carried out in the presence of a fusogen, such as polyethylene glycol having a molecular weight of about 1000 to 6000 daltons, using a myeloma cell:spleen cell ratio of about 1:10 to about 10:1, preferably about 1:1. Balanced salt solutions containing about 30% to 60% (w/v), preferably 35% to 50% fusogen may be used as a fusion medium. The individual cell concentrations will typically be in the range of about $10^6$ to $10^8$, preferably $1-5 \times 10^7$ cells/ml. After the fusion, the cells are washed with fusogen-free medium to remove fusogen. They are then seeded in a selective medium, such as HAT medium (Littlefield, *Science*, 145:709-710 (1964)), to eliminate unhybridized parent cells and leave only hybrids that are resistant to the selective medium and possess the immortality of the myeloma parent. Culturing in the selective medium will normally take about 3 to 8 weeks.

Human monoclonal anti-idiotype antibodies may be made by similar procedures using an appropriate human tumor line and human anti-idiotype producing cells as fusion partners. Human tumor lines are described in European patent application 82301103.6. Human anti-idiotype-producing cells may be made by cultivating spleen cells in an idiotype-containing medium or by immunizing human subjects with idiotype and collecting antibody-producing cells from the immunized subject. Monoclonal anti-idiotype antibodies of other mammalian species may likewise be made.

Screening of Hybridoma Culture Media for Antibody Against Idiotype

The invention assay is used to screen hybridoma culture media for anti-idiotype secreting hybrids, particularly hybrids that secrete an anti-idiotype of the IgG class. It may also be used to determine the specificity of antibodies that react with the idiotype. This assay makes testing for monoclonal anti-idiotype antibodies easy relative to the prior method. It is sensitive enough to be used with a small sample of tumor cells from the patient (on the order of $10^8$ cells) and to detect anti-idiotype antibodies at levels down to about 10 ng/ml. It also permits large numbers of culture fluid samples to be screened rapidly.

The invention assay is a solid phase immunoassay. This type of assay is well known as is exemplified by the popular enzyme-linked immunosorbent assay (ELISA). The first step of the assay circumvents the need for preparing and purifying idiotype. It involves incubating a lysate of the patient's tumor cells with immobilized anti-human antibody that reacts with the idiotype but not with the analyte monoclonal antibody whereby the idiotype is selectively removed from the lysate by binding to the immobilized antibody.

The anti-human Ig reagent may be obtained from nonhuman species such as goat, horse, rabbit, pig, guinea pig, and the like. It may be polyclonal or monoclonal. Antigen binding fragments (Fab, Fab', F(ab')$_2$) of the anti-human Ig may be used if desired. When the analyte is a murine monoclonal antibody, cross reactants with mouse Ig may be removed from the anti-human Ig by affinity chromatography using a stationary phase of mouse Ig bound to an immunosorbent material. If desired, an anti-human Ig that is specific for a particular class of human Ig may be used. In this regard since the idiotype will typically be IgM it may be desirable to use an anti-human IgM serum. When the analyte is a human monoclonal anti-idiotype of the IgG class and the idiotype is of the IgM class, an anti-human IgM will be used.

The anti-human Ig reagent is adsorbed onto a protein immobilizing medium such as plates, tubes, or beads of a synthetic or natural immunosorbent material such as cellulose, agarose, cross-linked polysaccharides, polyvinylchloride, polystyrene, and the like. The adsorption may be carried out by coating the immobilizing medium with a solution of the anti-human Ig in a balanced salt solution, such as PBS or Hank's solution. The incubation temperature and time are not critical. Room temperature may be used for convenience. The incubation will typically run at least about four hr at such temperatures. The concentration of anti-human Ig in solution will usually be about 10 $\mu$g/ml. If the immobilized anti-human Ig is to be stored for extended periods, an antibacterial agent such as sodium azide should be added to the coating solution. Before the immobilized anti-human Ig is incubated with the tumor cell lysate it is post-coated with a protein, such as albumin, that does not react with the adsorbed anti-human Ig. The purpose of the post-coating is to block any remaining protein binding sites on the immobilizing medium that are not occupied by anti-human Ig. Such blocking prevents nonspecific adsorption of proteinaceous reagents used in subsequent steps of the assay.

The tumor cell lysate is prepared as follows. The malignant B cells are isolated from a biopsy specimen or peripheral blood from the patient and cultured for a short period, typically about 12 to 24 hr in a mammalian cell growth medium to remove any extraneous Ig carried over from the specimen or blood. The cells are then collected from the culture medium, washed, and suspended in an aqueous cytolytic buffer under conditions that inhibit degradation of the idiotype. The buffer will typically contain one or more cell membrane solubilizing agents and one or more protease inhibitors. The solubilizing agent will usually be present at a concentration of about 0.1 to 0.5% (v/v). Examples of solubilizing agents that may be used are Nonidet P40 detergent, Triton X-100 detergent, Lubrol PX detergent, or deoxycholate. The cells will normally be contacted with the buffer at a concentration of about $5 \times 10^6$ to $1 \times 10^7$ cells/ml at reduced temperatures, typically about 4° C. to about 10° C. for one-half to one hr with mild, occasional agitation. Following the lysis, cellular debris may be removed from the lysate by centrifugation.

The tumor cell lysate is incubated with the immobilized anti-human Ig under conditions that promote binding of the idiotype in the lysate to the immobilized anti-human Ig via the Fc portion of the idiotype. Room temperature may be used for convenience although lower temperatures (e.g., 4° C. to 10° C.) may be used if desired. The incubation time will typically vary between one to two hr. Following the incubation, unbound cell lysate material is removed from the incubation product (an immobilized anti-human Ig-idiotype complex). This procedure isolates sufficient idiotype to carry out the screening even though the idiotype constitutes an extremely low fraction (i.e., less than 1%) of the total protein in the lysate.

The next step in the assay is to incubate the test hybridoma culture medium with the immobilized anti-human Ig-tumor cell lysate incubation product. This step is carried out under conditions that promote binding between the immobilized complex and anti-idiotype antibodies in the hybridoma culture medium. The same incubation conditions as are used in the tumor cell lysate incubation may be used. Positive and negative controls are run in parallel with the test culture medium to test the specificity of any monoclonal anti-idiotype antibody in the test medium. A solution of monoclonal anti-idiotype antibody against another patient's cells or some other unreactive monoclonal antibody may be used as a negative control and a monoclonal anti-isotype antibody may be used as a positive control. In this step any monoclonal anti-idiotype antibody in the test culture medium will react with the immobilized complex to form a ternary complex consisting of immobilized anti-human Ig, idiotype, and monoclonal anti-idiotype. After the incubation, unbound hybridoma culture medium material is removed from the incubation product.

The third step of the assay is to incubate the ternary complex with a labeled antibody against the analyte monoclonal antibody. When the analyte monoclonal antibody is a murine antibody, a labeled anti-murine antibody, preferably one that does not cross react with human Ig, is used. Such cross reactants may be removed by affinity chromatography. The anti-murine antibody may be prepared by immunizing other mammalian species such as rabbit, goat and horse with murine Ig. When the analyte is a human monoclonal IgG and the idiotype is an IgM an anti-human IgG antibody that does not cross react with human IgM is used. Isotopic (e.g., $125_I$, $3_H$) or nonisotopic (e.g., enzyme, fluorescent, biotin-avidin complex, chemiluminescent) labels may be used. These labels may be incorporated or conjugated to the anti-mouse or anti-human IgG sera by known procedures. Labeled anti-mouse sera and anti-human IgG are available commercially. Enzyme labels are preferred because they provide high sensitivity and are relatively easy to read. When enzyme-labeled anti-mouse antibody is used an additional step between the incubation therewith and the detection step is required. It involves reacting the enzyme with an appropriate substrate to produce a spectrophotometrically detectable product. When biotin is employed the complex is reacted with avidin labeled with an isotope or enzyme. The incubation with the labeled antibody may be carried out using the same incubation conditions as are used in the first and second incubation in the assay.

It is within the scope of the invention to bind one or more nonlabeled sera to the immobilized ternary complex before binding the final labeled antibody to the multilayer complex. The use of such intermediate layers of antibody may permit signal amplification and/or enhance the specificity of the assay.

The particulars of the detection (reading) phase of the assay will depend upon the nature of the label involved. With enzyme labels, the reaction with the substrate produces a colored reaction product that may be observed visibly or with a spectrophotometer. When isotopic labels are used the product will be read with a radiation detector or counter. Fluorescent labeled complexes are read with fluorometers. The results obtained with the test culture medium will be compared to results obtained with positive and negative control tests to determine the presence and specificity of monoclonal anti-idiotype antibodies.

Hybridoma Expansion and Antibody Production

Hybridomas that are positive for anti-idiotype production in the invention assay will typically be subcloned under limiting dilution conditions and grown in vitro in a suitable growth medium or in vivo such as in the ascites of mice. The product antibodies are collected from the culture medium or the mice, as the case may be, and may be purified by known techniques such as ammonium sulfate precipitation, ion exchange chromatography, affinity chromatography, ultrafiltration, or microfiltration before being used in therapy or diagnosis.

EXAMPLES

The invention method is further illustrated by the following examples. These examples are not intended to limit the invention in any manner.

The materials and methods used in the examples were as follows.

MATERIALS

Affinity purified goat anti-human Ig (polyvalent), (Tago Inc., Burlingame, CA) was used as the anti-human Ig reagent. All cross reactions with mouse Ig were removed by passing the antiserum over a mouse-Ig-Sepharose ® immunosorbent.

Horseradish peroxidase conjugated goat anti-mouse IgG or biotin conjugated goat anti-mouse IgG (Tago Inc., Burlingame, CA) was used as the labeled anti-mouse antibody reagent. These affinity purified antibodies were passed over a Normal-Human-Serum-Sepharose column to eliminate crossreactivity with human Ig.

The composition of the lysis buffer that was used was as follows: PBS, (0.14 M NaCl—0.02 M NaHPO$_4$, pH 7.4), 1 m M ethylenediaminetetraacetic acid (EDTA), 2 m M phenylmethylsulfonylfluoride, and 0.5% (v/v) Nonidet P40 detergent.

Tumor cell lysates were prepared as follows. Malignant cells were isolated from peripheral blood and cultured for 24 hours in RPMI containing 15% fetal calf serum in order to remove Ig carried over from the patient's serum. Cells were then collected and washed three times in PBS. Finally, the cells were resuspended at $5 \times 10^6$ cells/ml in lysis buffer. This mixture was incubated on ice for 30 min with occasional agitation. Cell debris was removed by centrifugation (Sorvall centrifuge, 15000 rpm for 60 min at 4° C.).

The substrate solution was composed of 10 ml citric acid buffer, pH4, 100 μl of a 15 mg/ml aqueous solution of 2,2'amino-di-(3-ethyl-benzothiazolin-sulfonic acid), and 3.3 μl $H_2O_2$, 30%.

The wash solution used was 0.05% (v/v) Nonidet P40 detergent in normal saline.

Candidate anti-idiotype-producing hybridomas were prepared from the B cell tumors of ten patients by the procedure of U.S. Ser. No. 322,377, supra, as modified by Mayumi, M. et al, supra.

The assays were carried out in Immulon ® microtiter plates. The surfaces of the wells served as the immobilizing medium.

METHODS

Coating the microtiter plate wells with the anti-human Ig.

50 μl of a PBS solution of the goat anti-human Ig (10 μg/ml) in PBS was pipetted into the flat bottom wells of the microtiter plate. The plate was covered with Parafilm and allowed to stand for 24 hr at 4° C. The coating solution was then removed and the wells were filled with a 2% solution of bovine serum albumin (BSA) in PBS. After 30 min, the BSA solution was removed and the plate was washed three times with wash solution.

Incubation with tumor cell lysate.

Fifty μl of the cell lysate supernatant was injected into each well and the plate was kept at room temperature for one hr with continuous gentle agitation. The unbound cell lysate material was then removed and the plate was washed five times with wash solution.

Incubation with hybridoma culture fluid.

Fifty μl of culture supernatant was pipetted into each well. The reaction was allowed to proceed for at least one hr at room temperature with gentle agitation. Positive and negative controls (i.e., a mouse monoclonal anti-idiotype antibody against another patient's cells as negative control; a monoclonal anti-human IgM antibody as positive control) were carried out in parallel.

Unbound supernatant was removed after the reaction and the plate was washed five times.

Incubation with labeled anti-mouse Ig.

Prior to use the "working dilution" of the labeled reagent was determined by titration. Fifty μl of peroxidase labeled anti-mouse IgG diluted in 1% BSA-PBS was pipetted into each well. The plate was kept at room temperature for 1 hr. Unbound labeled antibody was then removed and the plate was once again washed.

Reaction with substrate.

One hundred μl of fresh substrate solution was added to each well followed by incubation in the dark at room temperature. When the positive control wells show the desired color, the plate was placed in a photometer apparatus (Dynatech). The color reaction may be stopped by the addition of 25 μl of 10% sodium dodecyl sulfate. Readings were reported in terms of optical density (OD).

Results.

FIG. 1 is a graph of OD readings versus dilution showing curves of assays using the tumor cell lysate of a patient (identified as x) and (a) hybridoma culture fluid suspected of containing antibodies against the same patient's idiotype (b) the anti-isotype antibody (anti-human IgM) reagent (c) a BSA-PBS solution or (d) hybridoma culture media containing antibodies against other patients' idiotypes. As shown the assay was positive for (a) and (b) and negative for (c) and (d).

Figure 2:
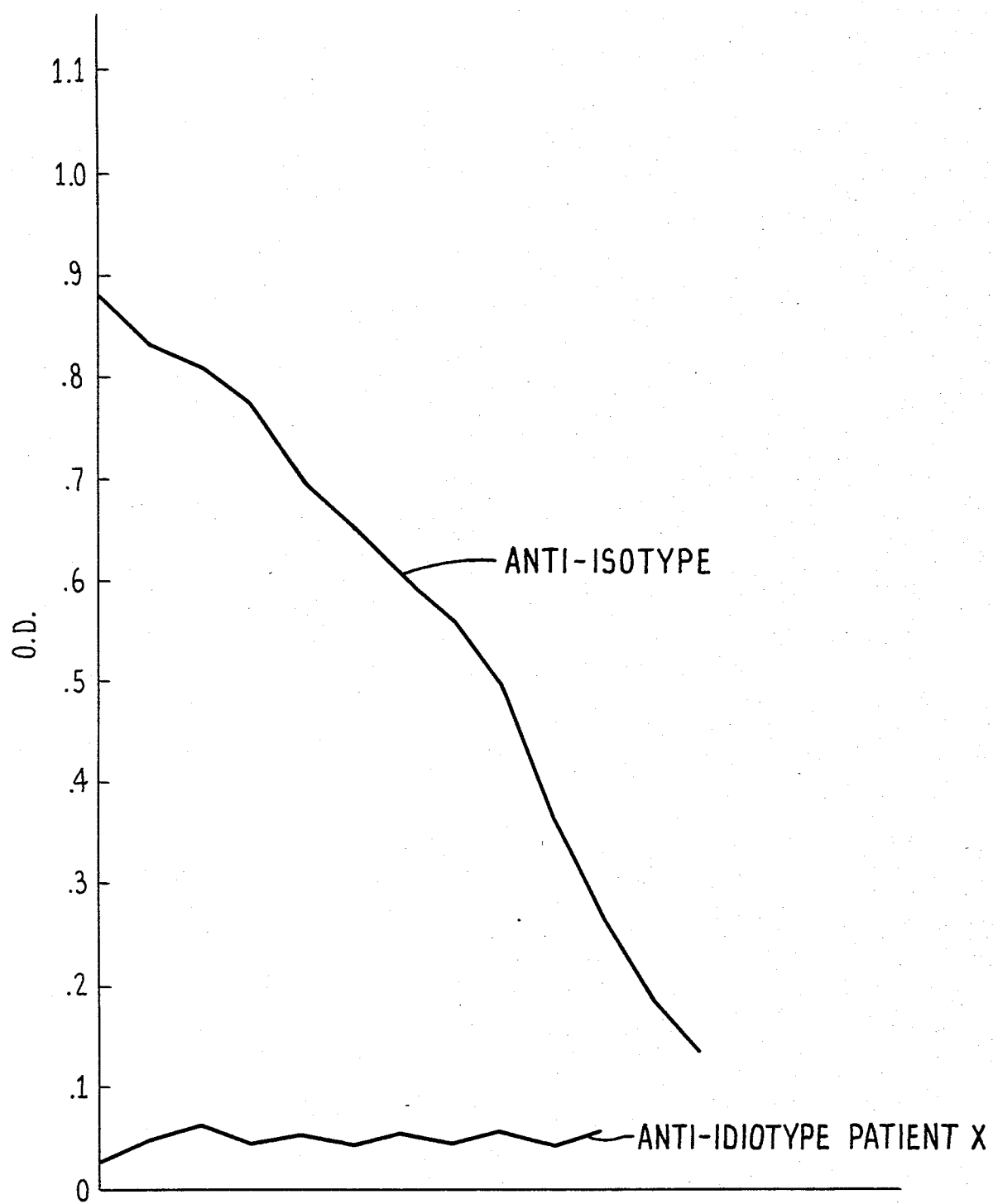
FIG. 2 is a graph illustrating the specificity of the assay.

FIG. 2 is a graph of OD readings versus dilution showing curves of assays using the tumor cell lysate of another patient and (a) the anti-isotype antibody reagent or (b) the hybridoma culture fluid containing monoclonal antibody against patient x idiotype. As expected, the anti-isotype assay was positive and the patient x assay was negative.

Figure 3:
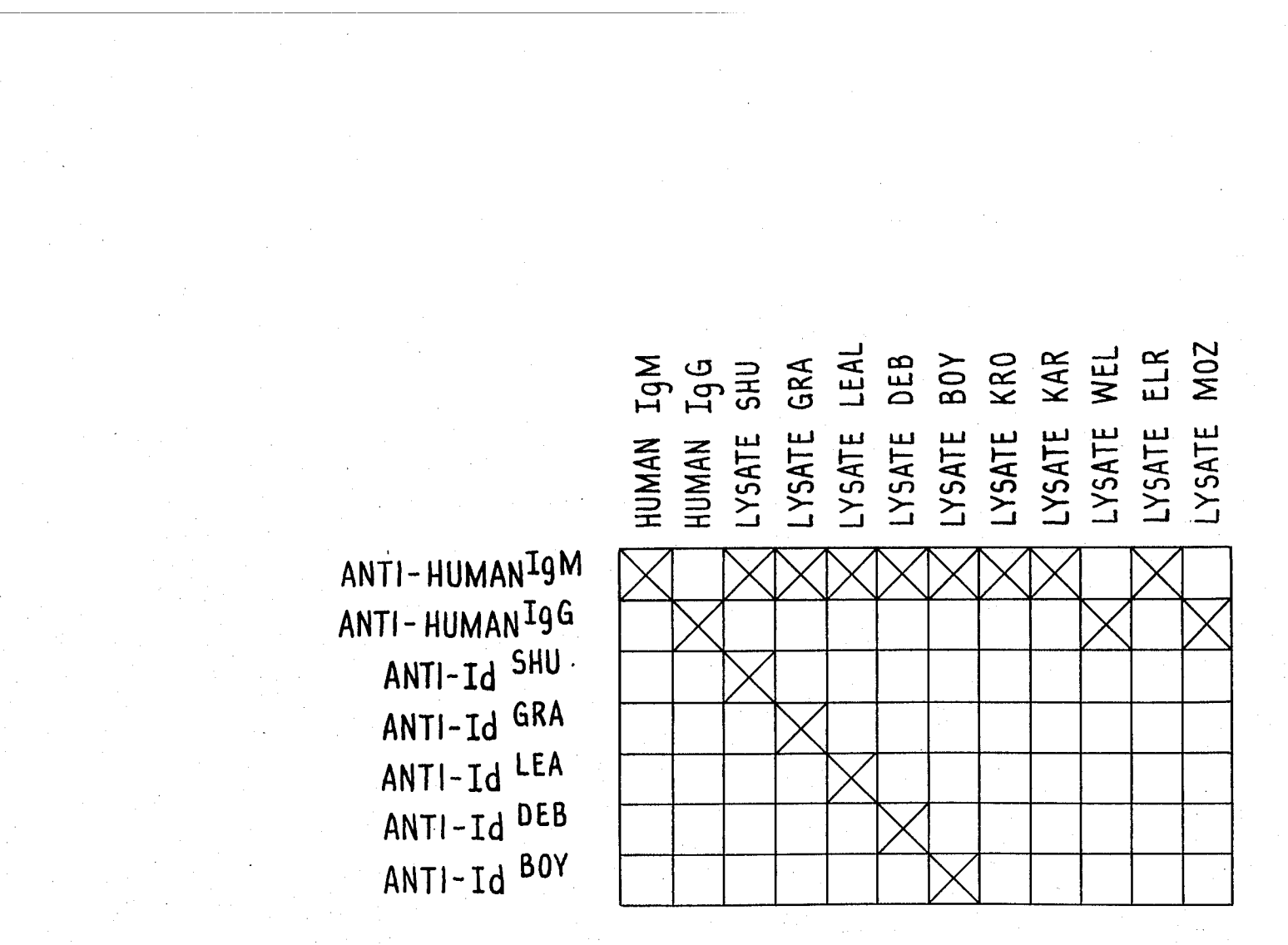

FIG. 3 is a chart that illustrates the specificity of the assay. The left hand side of the chart lists the antibodies tested: an anti-human IgM monoclonal antibody, an anti-human IgG monoclonal antibody, and monoclonal antibodies against the idiotypes of five of the patients. Across the top of the chart are listed the antigen targets: human IgM, human IgG, and the tumor cell lysates of the 10 patients. Reactions are indicated by an X, no reaction is indicated by a blank. This chart shows that the idiotypes of patients SHU, GRA, LEAL, DEB, BOY, KRO, KAR and ELR are IgMs whereas those of patients WEL and MOZ are IgGs. It also shows that the five monoclonal anti-idiotypes reacted only with their corresponding tumor cell lysates and not with lysates of other patients.

Modifications of the above describes modes for carrying out the invention that are obvious to those of skill in the fields of medicine, immunology and related fields are intended to be within the scope of the following claims.

We claim:

1. An immunoassay for detecting a monoclonal antibody that binds specifically to the surface IG of a human B cell tumor in a hybridoma culture medium suspected of containing the monoclonal antibody comprising:
   (a) incubating a lysate of cells of the tumor with an antibody immobilized on a solid phase that binds to the surface Ig but not to the monoclonal antibody under conditions that promote binding of the surface Ig to the immobilized antibody;
   (b) removing unbound lysate material from the solid phase;
   (c) incubating the solid phase with the hybridoma culture medium under conditions that promote binding of any monoclonal antibody in the culture medium to immobilized antibody-surface Ig complex;
   (d) removing unbound culture medium material from the solid phase;
   (e) incubating the solid phase with a labeled antibody that binds to the monoclonal antibody under conditions that promote binding of the labeled antibody to immoblized antibody-surface Ig-monoclonal antibody complex;
   (f) removing unbound labeled antibody from the solid phase;
   (g) detecting the presence of labeled complex in the product of step (f).

2. The immunoassay of claim 1 wherein the monoclonal antibody is a murine monoclonal IgG antibody and the labeled antibody is an anti-mouse antibody.

3. The immunoassay of claim 2 wherein the immobilized antibody is one that does not bind to murine Ig.

4. The immunoassay of claim 3 wherein the immobilized antibody is goat antibody.

5. The immunoassay of claim 1 wherein the surface Ig is an IgM, the monoclonal antibody is a human IgG, the immobilized antibody is an anti-human IgM antibody and the labeled antibody is an anti-human IgG antibody that does not bind to human IgM.

6. The immunoassay of claim 1 wherein the material on which the immobilized antibody is immobilized is post-coated with a protein that does not bind to mammalian Ig.

7. The immunoassay of claim 1 wherein the labeled antibody is one that does not bind to the immobilized antibody.

8. The immunoassay of claim 1 wherein the labeled antibody is an enzyme labeled antibody.

9. The immunoassay of claim 2 wherein the immobilized antibody is one that does not bind to murine Ig, the material on which the antibody against human Ig is immobilized is post-coated with a protein that does bind to mammalian Ig, and the labeled antibody against mouse Ig is an enzyme labeled antibody that does not bind to human Ig.

10. The immunoassay of claim 9 wherein the immobilized antibody and the enzyme labeled antibody are goat antibodies.

* * * * *